United States Patent [19]

Davie et al.

[11] Patent Number: 5,399,684
[45] Date of Patent: Mar. 21, 1995

[54] DNA SEQUENCES EXPRESSING MAMMALIAN ALPHA-1-ANTITRYPSIN

[75] Inventors: Earl W. Davie, Bellevue; Kotoku Kurachi, Seattle, both of Wash.; Savio L. C. Woo; Chandra Thirumalachary, both of Houston, Tex.

[73] Assignee: Washington Research Foundation, Seattle, Wash.

[21] Appl. No.: 86,442

[22] Filed: Jul. 2, 1993

Related U.S. Application Data

[63] Continuation of Ser. No. 979,556, Nov. 18, 1992, abandoned, which is a continuation of Ser. No. 666,450, Mar. 11, 1991, abandoned, which is a continuation of Ser. No. 398,288, Aug. 22, 1989, abandoned, which is a continuation of Ser. No. 246,912, Sep. 16, 1988, abandoned, which is a continuation of Ser. No. 133,190, Dec. 15, 1987, abandoned, which is a continuation of Ser. No. 22,543, Mar. 3, 1987, abandoned, which is a continuation of Ser. No. 638,980, Feb. 7, 1984, abandoned, which is a continuation of Ser. No. 380,310, May 20, 1982, abandoned.

[51] Int. Cl.⁶ ............... C12N 15/09; C12N 15/12; C12N 15/15
[52] U.S. Cl. ............... 536/23.5; 435/240.1; 435/252.3; 435/320.1
[58] Field of Search ............... 435/69.2, 91.1, 172.1, 435/172.3, 240.1, 240.2, 252.3–252.35, 320.1; 536/23.5; 530/380; 935/11, 14, 29, 34, 66–75

[56] References Cited

PUBLICATIONS

Wallace et al; Nucleic Acids Res. 6: 3543 (1979).
Suggs et al; Proc. Natl. Acad. Sci. USA 78: 6613 (1981).
Kurachi et al, "Cloning and sequence of cDNA coding for alpha–1–antitrypsin", Proc. Natl. Acad. Sci. USA 78: 6826 (1981).
Woo et al, "the human alpha–1–antitrypsin gene: its sequence homology and structural comparison with the chicken ovalbumin gene", Chem. Abstr. 98: 120615z (1983) of UCLA Symp. Mol. Cell. Biol. 26(Gene Regul.), 55–64 (1982).
Clissold et al, "Molecular cloning of cDNA sequences transcribed from mouse liver endoplasmic reticulum poly(a)mRNA", Gene 15: 225 (1981).
Houghton et al, "the amino–terminal sequence of human fibroblast interferon as deduced from reverse transcripts obtained using synthetic olignucleotide primers", Nucleic Acids Res. 8: 1913 (1980).
Wilson et al:"Isolation of human alpha–1 anti trypsin mRNA from liver tissue for molecular cloning" in J. Supramol. Struct. Cell. Biochem. (Suppl. 5), (1981), 421 presented at the ICN–University of California at Los Angeles, Mar. 15–20, 1981.
Clissold et al: Biol. Abstr. 73, 60806 (1982) abstract of Gene 15, 225 (1981).
Morii et al, "Human alpha–1–antitrypsin, Characterization and N– and C– terminal sequences", J. Biochem. 83: 269 (1978).
Roberts et al, "A general method for maximizing the expression of a cloned gene", Proc. Natl. Acad. Sci. USA 76: 760 (1979).
Goeddel et al; Nucleic Acids Res. 8: 4057 (1980).

*Primary Examiner*—James Martinell
*Attorney, Agent, or Firm*—Christensen, O'Connor, Johnson & Kindness

[57] ABSTRACT

DNA sequences to mammalian $\alpha_1$-antitrypsin are provided which can be used for expression of mammalian $\alpha_1$-antitrypsin.

4 Claims, 11 Drawing Sheets

```
5'
G G G G G G G G G G G G G G A G T G A A T C G A C A
                        -24
                        Met Pro Ser Ser Val Ser Trp Gly Ile Leu
                        ATG CCG TCT TCT GTC TCG TGG GGC ATC CTC
                        +1                  -20          10      30

Leu Leu Ala Gly Leu Cys Cys Leu Val Pro
CTG CTG GCA GGC CTG TGC TGC CTG GTC CCT
-10              40       -1  1          50              60

Val Ser Leu Ala Glu Asp Pro Gln Gly Asp
GTC TCC CTG GCT GAG GAT CCC CAG GGA GAT
            70                  10          80              90

Ala Ala Gln Lys Thr Asp Thr Ser His His
GCT GCC CAG AAG ACA GAT ACA TCC CAC CAT
                100             110             120
```

FIGURE 1A

```
                    20
Asp Gln Asp His Pro Thr Phe Asn Lys Ile
GAT CAG GAT CAC CCA ACC TTC AAC AAG ATC
            130         140         150

30
Thr Pro Asn Leu Ala Glu Phe Ala Phe Ser
ACC CCC AAC TTG GCT GAG TTC GCC TTC AGC
            160         170         180

40
Leu Tyr Arg Gln Leu Ala His Gln Ser Asn
CTA TAC CGC CAG CTG GCA CAC CAG TCC AAC
            190         200         210

50
Ser Thr Asn Ile Phe Phe Ser Pro Val Ser
AGC ACC AAT ATC TTC TTC TCC CCA GTG AGC
            220         230         240
```

FIGURE 1B

```
Ile Ala Thr Ala Phe Ala Met Leu Ser Leu
ATC GCT ACA GCC TTT GCA ATG CTC TCC CTG
        60              260             270
                        250

Gly Thr Lys Ala Asp Thr His Asp Glu Ile
GGA ACC AAG GCT GAC ACT CAC GAT GAA ATC
        70              290             300
                        280

Leu Glu Gly Leu Asn Phe Asn Leu Thr Glu
CTG GAG GGC CTG AAT TTC AAC CTC ACG GAG
        80              320             330
                        310

Ile Pro Glu Ala Gln Ile His Glu Gly Phe
ATT CCG GAG GCT CAG ATC CAT GAA GGC TTC
        90              350             360
                        340
```

FIGURE 1C

```
                100
Gln  Glu  Leu  Leu  Arg  Thr  Leu  Asn  Gln  Pro
CAG  GAA  CTC  CTC  CGT  ACC  CTC  AAC  CAG  CCA
         370            380           390

110
Asp  Ser  Gln  Leu  Gln  Leu  Thr  Thr  Gly  Asn
GAC  AGC  CAG  CTC  CAG  CTG  ACC  ACC  GGC  AAT
         400            410           420

120
Gly  Leu  Phe  Leu  Ser  Glu  Gly  Leu  Lys  Leu
GGC  CTG  TTC  CTC  AGC  GAG  GGC  CTG  AAG  CTA
         430            440           450

130
Val  Asp  Lys  Phe  Leu  Glu  Asp  Val  Lys  Lys
GTG  GAT  AAA  GTT  TTT  GGA  GGA  TGT  TAA  AAA  AG
         460            470           480
```

FIGURE 1D

```
                                         140
Leu  Tyr  His  Ser  Glu  Ala  Phe  Thr  Val  Asn
T T G  T A C  C A C  T C A  G A A  G C C  T T C  A C T  G T C  A A C
              490            500            510

150
Phe  Gly  Asp  Thr  Glu  Glu  Ala  Lys  Lys  Gln
T T C  G G G  G A C  A C C  G A A  G A G  G C C  A A G  A A A  C A G
              520            530            540

160
Ile  Asn  Asp  Tyr  Val  Glu  Lys  Gly  Thr  Gln
A T C  A A C  G A T  T A C  G T G  G A G  A A G  G G T  A C T  C A A
              550            560            570

170
Gly  Lys  Ile  Val  Asp  Leu  Val  Lys  Glu  Leu
G G G  A A A  A T T  G T G  G A T  T T G  G T C  A A G  G A G  C T T
              580            590            600
```

```
                180
Asp Arg Asp Thr Val Phe Ala Leu Val Asn
GAC AGA GAC ACA GTT TTT GCT CTG GTG AAT
610                 620                 630

190
Tyr Ile Phe Phe Lys Gly Lys Trp Glu Arg
TAC ATT CTT CTT AAA GGC AAA TGG GAG AGA
640                 650                 660

200
Pro Phe Glu Val Lys Asp Thr Glu Glu Glu
CCC TTT GAA GTC AAG GAC ACC GAG GAA GAG
670                 680                 690

210
Asp Phe His Val Asp Gln Val Thr Thr Val
GAC TTC CAC GTG GAC CAG GTG ACC ACC GTG
700                 710                 720
```

FIGURE 1G

```
                                    220
Lys Val Pro Met Met Lys Arg Leu Gly Met
AAG GTG CCT ATG ATG AAG CGT TTA GGC ATG
        730                 740         750

230
Phe Asn Ile Gln His Cys Lys Lys Leu Ser
TTT AAC ATC CAG CAT TGT AAG AAG CTG TCC
        760                 770         780

240
Ser Trp Val Leu Leu Met Lys Tyr Leu Gly
AGC TGG GTG CTG CTG ATG AAA TAC CTG GGC
        790                 800         810

250
Asn Ala Thr Ala Ile Phe Phe Leu Pro Asp
AAT GCC ACC GCC ATC TTC TTC CTG CCT GAT
        820                 830         840
```

```
       260
Glu Gly Lys Leu Gln His Leu Glu Asn Glu
GAG GGG AAA ACT ACA GCA CCC TGG AAA ATG AA
            850         860         870

270
Leu Thr His Asp Ile Ile Thr Lys Phe Leu
CTC ACC CAC GAT ATC ATC ACC AAG TTC CTG
            880         890         900

280
Glu Asn Glu Asp Arg Arg Ser Ala Ser Leu
GAA AAT GAA GAC AGA AGG TCT GCC AGC TTA
            910         920         930

290
His Leu Pro Lys Leu Ser Ile Thr Gly Thr
CAT TTA CCC AAA CTG TCC ATT ACT GGA ACC
            940         950         960
```

FIGURE 1H

```
            300
Tyr Asp Leu Lys Ser Val Leu Gly Gln Leu
TAT GAT CTG AAG AGC GTC CTA GGT CAA CTG
            970         980         990

310
Gly Ile Thr Lys Val Phe Ser Asn Gly Ala
GGC ATC ACT AAG GTC TTC AGC AAT GGG GCT
            1000        1010        1020

320
Asp Leu Ser Gly Val Thr Glu Glu Ala Pro
GAC CTC TCC GGG GTC ACA GAG GAG GCA CCC
            1030        1040        1050

330
Leu Lys Leu Ser Lys Ala Val His Lys Ala
CTG AAG CTC TCC AAG GCC GTG CAT AAG GCT
            1060        1070        1080
```

FIGURE 1I

```
              340
Val Leu Thr Ile Asp Glu Lys Gly Thr Glu
GTG CTG ACC ATC GAC GAG AAA GGG ACT GAA
1090          1100          1110

350
Ala Ala Gly Ala Met Phe Leu Glu Ala Ile
GCT GCT GGG GCC ATG TTT TTA GAG GCC ATA
1120          1130          1140

360
Pro Met Ser Ile Arg Pro Glu Val Lys Phe
CCA TGT CTA TCC GCC CGA GGT CAA GTT C
1150          1160          1170

370
Asn Lys Pro Phe Val Phe Leu Met Ile Glu
AAC AAA CCC TTT GTC TTC TTA ATG ATT GAA
1180          1190          1200
```

FIGURE 1J

```
              380
Gln Asn Thr Lys Ser Pro Leu Phe Met Gly
C A A A A T A C C A A G T C T C C C C T T C A T G G G A
              1210              1220              1230
              390                   394
Lys Val Val Asn Pro Thr Gln Lys STOP
A A A G T G G T G A A T C C C A C C C A A A A A T A A C T G
              1240              1250
C C T C T C G C T C C T C A A C C C C C C C C C C C
                                                  3'
```

FIGURE 1K

DNA SEQUENCES EXPRESSING MAMMALIAN ALPHA-1-ANTITRYPSIN

This invention was made with government support under grants HL16919 and HL00404 awarded by the National Institutes of Health. The government has certain rights in the invention.

This application is a continuation application based on prior application Ser. No. 07/979,556, filed on Nov. 18, 1992, now abandoned, which is a continuation application based on prior application Ser. No. 07/666,450, filed on Mar. 11, 1991, (now abandoned), which is a continuation of Ser. No. 07/398,288, filed on Aug. 22, 1989, (now abandoned), which is a continuation of Ser. No. 07/246,912, filed Sep. 16, 1988, (now abandoned), which is a continuation of Ser. No. 07/133,190, filed Dec. 15, 1987, (now abandoned), which is a continuation of Ser. No. 07/022,543, filed Mar. 3, 1987, (now abandoned), which is a continuation of Ser. No. 06/638,980, filed Feb. 7, 1984, (now abandoned) which is a continuation of Ser. No. 06/380,310, filed May 20, 1982, (now abandoned).

BACKGROUND OF THE INVENTION

1. Field of the Invention $\alpha_1$-Antitrypsin is an important protease inhibitor present in mammalian blood. Its major physiological function appears to be the inhibition of neturophil elastase, a potent protease that hydrolyzes structural proteins. It also inhibits many other serine proteases.

A low level of $\alpha_1$-antitrypsin in the blood is often associated with chronic obstructive pulmonary emphysema and infantile liver cirrhosis. At present, more than 30 different genetic variants have been identified. Several of these are associated with low concentrations of the inhibitor in the blood.

The normal plasma level of $\alpha_1$-antitrypsin is about 2 mg/ml. Under most inflammatory conditions, an acute-phase response is initiated and the concentration of $\alpha_1$-antitrypsin is substantially increased. In order to study $\alpha_1$-antitrypsin deficiency at the molecular level and examine the mechanism of the acute phase response, it would be desirable to have pure $\alpha_1$-antitrypsin polypeptide. The $\alpha_1$-antitrypsin polypeptide could be used for the formation of antibodies to the numerous determinant sites to provide for detection of variants in the blood, as a ligand in assays for $\alpha_1$-antitrypsin, and for introduction into a host having $\alpha_1$-antitrypsin deficiency.

2. Description of the Prior Art

Shochat, et al., J. Biol. Chem. (1978), 253:5630–5634; Morii, et al., J. Biochem. (1978), 83:269–277; Carrell, et al., Biochem. Biophys. Res. Conunun. (1979), 91:1032–1037 Mega, et al., Biol. Chem. (1980), 255:4057–4061; and Crawford, Arch. Blochem. Biophys. (1973), 156:215–222; have reported various characteristics of $\alpha_1$-antitrypsin. Kurachi, et al., Proc. Natl. Acad. Sci. U.S.A. (1981), 78:6826–6830, and Chandra, et al., Blochem. Biophys. Res. Comm. (1981), 103:751–758, describe cloning and sequencing of cDNA coding for $\alpha_1$-antitrypsin.

SUMMARY OF THE INVENTION

DNA sequences, including cDNA and recombinant DNA capable of expressing mammalian $\alpha_1$-antitrypsin are provided, as well as compositions and methods for producing the polypeptide chain of $\alpha_1$-antitrypsin. $\alpha_1$-Antitrypsin polypeptide made by recombinant DNA is provided.

BRIEF DESCRIPTION OF THE DRAWINGS

FIGS. 1A–1K set forth the human $\alpha_1$-antitrypsin cDNA discussed in the specification.

DESCRIPTION OF THE SPECIFIC EMBODIMENTS

DNA sequences capable of expression of polypeptides having mammalian $\alpha_1$-antitrypsin biological activity are provided. The sequences can be used for introduction into a host cell to enhance the production of products having $\alpha_1$-antitrypsin activity. The DNA sequences include DNA sequences having exons and introns free of their normal flanking regions, messenger RNA which has been matured and is capped and includes a polyA 3' chain, cDNA obtained by reverse transcribing mRNA and the combination of the DNA with DNA sequences, which provide regulatory signals for expression, replication, amplification, and regulated response to a variety of conditions and reagents.

The expression products of the nucleic acid sequences are polypeptides having $\alpha_1$-antitrypsin activity, in that the compounds inhibit elastase by forming an equimolar complex of the enzyme and the inhibitor with an association rate constant of greater than about $10^6$ per mole-sec. The compounds are derived from mammals, particularly primates, such as baboon and human. The chromosomal DNA fragment encoding $\alpha_1$-antitrypsin is less than about 10 kb, usually less than about 9 kb. The approximate sizes of the exon regions I, II, III, and IV are, respectively, about 0.71, 0.33, 0.13, and 0.2 kb's in length. The sizes of the introns A, B, and C are, respectively, about 1.45, 1.15, and 0.8 kb's, and the three introns are generally located within the 5' half of the DNA. The cDNA encoding $\alpha_1$-antitrypsin is about 1.182 kb's in length. The mature mRNA encoding human $\alpha_1$-antitrypsin is about 1.4 kb's in length.

The DNA sequences may be used in a variety of ways. Where chromosomal DNA is employed for transformation of host cells which are capable of recognizing the intron borders and providing for the mature mRNA, the DNA may be calcium precipitated in accordance with conventional ways and used for transformation of primate cells. For the most part, cells which can be stably maintained in vitro are cancerous and various cancerous lines may be employed for transformation. Particularly, cells of hepatic origin; e.g., hepatomas, may be employed. One may then select for transformed cells overproducing $\alpha_1$-antitrypsin.

Rather than using bare DNA, cDNA obtained by reverse transcription of mature mRNA may be inserted into a wide variety of vectors for introduction into a host for expression of $\alpha_1$-antitrypsin. The particular vector will depend upon the host and other considerations affecting the efficiency of production of the $\alpha_1$-antitrypsin. Hosts which may be employed for the production of $\alpha_1$-antitrypsin include unicellular microorganisms, such as the prokaryotes (e.g. bacterial), and eukaryotes, such as fungi, (e.g. yeast), algae, protozoa, and the like. Vectors are available for cloning, expression, for amplification of genes, as well as providing for external controls, such as temperature, heavy metal ions, or the like.

Methods of introducing DNA into an organism and providing for amplification of genes encoded into such DNA may be found in PCT International Application Nos. US 81/00239 and US 81/00240. The choice of vector, regulatory signals, or other control systems will be primarily a matter relating to convenience, availability, fermentation equipment, economics, and intended use of the product. The aforementioned PCT applications provide for a generalized description of hybrid DNA technology, which technology is incorporated herein by reference.

The primate gene for $\alpha_1$-antitrypsin can be obtained by instituting hepatic local inflammation in a primate, then sacrificing the primate and isolating the liver. Polysomes are then obtained as described in the literature, and the polysomes synthesizing nascent $\alpha_1$-antitrypsin enriched by immunoprecipitation. (See Chandra et al., (1981) supra.) After analysis by mRNA-dependent cell-free translation employing reticulocytelysate, the desired cDNA would be obtained from the mRNA-enriched preparation. The cDNA is then restriction mapped and superfluous sequences removed or the cDNA is tailed, for example, a polydG-polydC tail, and then inserted into the cohesive ends of a vector. Based on the sequences, the cDNA may be modified in a variety of ways. Superfluous nucleotides, not involved in coding for $\alpha_1$-antitrypsin, may be removed by primer repair. See, for example, Goeddel, et al., Nucl. Acids Res. (1980), 8:4057–4074; Razin, et al., Proc. Natl. Acad. Sci. USA (1978), 75:4268–4270; and Wallace, et al., Science (1980), 209:1396–1400.

For primer repair, a synthetic single-stranded DNA oligomer is prepared which is complementary to the 3'-terminus of the coding ("sense") strand of the gene encoding the $\alpha_1$-antitrypsin. The cDNA is denatured and the DNA oligomer hybridized to the coding strand. The hybrid is then treated with T4 DNA polymerase or E coli DNA polymerase large ("Klenow") fragment, so that a double strand is obtained where the coding strand has the ATG codon as the initial 3 nucleotides.

Alternatively, instead of including the leader sequence, one may use in vitro mutagenesis and prepare a synthetic DNA oligomer which replaces the Ala codon at −1 with the Met codon ATG. As the first step in this process, one would prepare a synthetic DNA oligomer, including at least the following sequence: GAC-TAGCTC, normally having not more than about six more nucleotides at the 5' end and at least about three nucleotides at the 3' end of the oligomer complimentary to the nucleotide of the coding strand of the $\alpha_1$-antitrypsin gene. After hybridizing the coding strand with the oligomer, the mismatched hybrid will then be treated with the same polymerase indicated above, so that the resulting double-stranded DNA would have a blunt-end terminus beginning with the nucleotides of the oligomer. In this way, the resulting dsDNA could be inserted into an expression vector, downstream from an appropriate promoter, and ribosomal start site, so that expression would be initiated at the synthetically created Met codon. As appropriate, linkers may be used to provide for cohesive ends or, alternatively, the DNA sequence may be blunt end ligated into the expression vector.

An alternative method would be to cleave the DNA fragment containing the sequence encoding for $\alpha_1$-antitrypsin intact and then, by employing an exonuclease, such as Bal 31, and by chewing back the terminal residues, one obtains a heterogeneous mixture of fragments. By timing the digestion, based on the number of nucleotides which must be removed, one can obtain fragments which will have the ATG codon in appropriate juxtaposition with a ribosomal start site, when such fragments are inserted into an expression vector. Initially, one may introduce the fragments into a cloning vector and, by employing appropriate probes, select for the clone having the desired fragments.

A preferred way is to follow the procedure of Hitzeman et al., Nature (1981) 293:717–722, which disclosure is incorporated herein by reference. By restricting with BamHI, an intact fragment encoding for $\alpha_1$-antitrypsin is obtained except for the first two codons encoding Met and Glu. By ligating a linker having the nucleotides encoding the amino acids to the $\alpha_1$-antitrypsin frament, the entire $\alpha_1$-antitrypsin sequence may be inserted into an expression vector for expression.

In expressing the $\alpha_1$-antitrypsin, one may retain the secretory signal leader sequence or remove such leader sequence, depending upon the host. Where a higher order host is employed and the leader peptide is retained, the host secretes the $\alpha_1$-antitrypsin with removal of the leader peptide.

Various vectors may be employed, such as plasmids, cosmids, or viruses. The expression vectors may conveniently be shuttle vectors, which allow for amplification in a prokaryote with expression in a eukaryote. Therefore, one would require replicons for both eukaryotes and prokaryotes in the vector. Secondly, one can provide for a wide variety of markers, such as cytotoxic resistance, viral immunity, prototrophy in an auxotrophic host, and the like. Conveniently, antibiotic resistance can be employed as a useful marker. Other features of the vector may include homologous sequences with the host gene to provide for integration of the $\alpha_1$-antitrypsin gene into the chromosome of the host. If desired, minichromosomes may be employed as described by Clarke and Carbon, PNAS USA (1980), 77:2173–2177; and Clarke and Carbon, Nature (1980), 287:504–509.

The human $\alpha_1$-antitrypsin cDNA is set forth in the FIGS. 1A–1K.

The gene for the human -antitrypsin is of about 5 kb. The polynucleotide coding for the $\alpha_1$-antitrypsin, including the f-Met codon and leader sequence, is 1254 nucleotides, which includes 72 nucleotides involved with the leader sequence, as compared with about 1400 nucleotides for the mature messenger RNA. The mature human $\alpha_1$-antitrypsin has 394 amino acids, as set forth in the prior sequence.

In order to describe the manner in which the DNA sequence for human $\alpha_1$-antitrypsin and baboon $\alpha_1$-antitrypsin were developed, the following examples are offered by way of illustration and not by way of limitation.

EXPERIMENTAL

Overlapping Genomic $\alpha_1$-Antitrypsin Clones

A total of 16 independent phage isolates were obtained when $2 \times 10^6$ plaques from the human genomic DNA library (Lawn, et al., Cell (1978), 15:1156–1174) were screened using the baboon $\alpha_1$-antitrypsin cDNA clone (Chandra, et al., Biochem. Biophys. Res. Comm. (1981), 103:751–758) as a hybridization probe. Subsequent analysis of the 16 isolates indicated that they originated from four independent clones. The four clones, labeled aAT135, aAT35, aAT80 and aAT101, were analyzed by restriction mapping and Southern hybridization using as probes an Mbo II fragment of pBalal DNA, which contains the 3' terminal region of the baboon cDNA (Chandra, et al., ibid.) and an Hha I fragment of pBaαla2 DNA which is a baboon cDNA clone lacking only about 100 nucleotides at the 5' end of the mRNA (Kurachi, et al., PNAS USA (1981), 78:6826–6830). These results have established the orientation of the human $\alpha_1$-antitrypsin gene and have indicated that the entire gene may reside within a 9.6 kb Eco RI DNA fragment in the human genome.

Mosaic Structure of the Human $\alpha_1$-Antitrypsin Gene

The overall structure of the human $\alpha_1$-antitrypsin gene was established by electron microscopic examination of hybrid molecules formed between the cloned chromsomal DNA and baboon $\alpha_1$-antitrypsin mRNA. The mature mRNA consists of approximately 1400 nucleotides. DNA was denatured thermally and hybrids were formed subsequently under conditions that favored RNA/DNA hybridization but not DNA/DNA reassociation. From the electron micrographs and line drawings, it was evident that there are three intervening DNA loops (introns) of various sizes within the human $\alpha_1$-antitrypsin gene. The poly(A) tract in the mRNA was clearly visible in the hybrid molecule, thereby confirming the orientation of the gene. When aAT135 DNA was cleaved with Eco RI prior to hybrid formation with the baboon mRNA, the smallest intervening DNA loop was very close to one end of the DNA molecule. Numonic measurements of the hybrid molecules have indicated that the approximate sizes of exon regions I, II, III, and IV are 0.71, 0.33, 0.13 and 0.27 kb's in length, respectively. The sizes of introns A, B, and C are 1.45, 1.15, and 0.8 kb's, respectively, and all three introns appear to be located within the 3' half of the mRNA.

In order to characterize the human chromosomal $\alpha_1$-antitrypsin gene in greater detail, the 9.6 kb Eco RI DNA fragment was subcloned into the Eco RI site of pBR322. The resulting clone, pAT9.6, was analyzed by restriction mapping and Southern hybridization. Four exon segments were identified within the 9.6 kb Eco RI DNA fragment using a combination of enzymes that do not cut the baboon $\alpha_1$-antitrypsin cDNA insert in pBaαla2 (Kurachi, et al. (1981), supra) These results confirmed the existence of three introns in the human $\alpha_1$-antitrypsin gene. The presence of only three introns in the peptide-coding region of the human chromosomal $\alpha_1$-antitrypsin gene was confirmed by DNA sequence analysis.

The 5' and 3' terminal sequences of the human $\alpha_1$-antitrypsin gene

Southern hybridization analysis between different portions of the baboon cDNA clone and humangeonomic fragments generated by digestion of pAT9.6 revealed DNA fragments which hybridize uniquely with either the 5' or the 3' end of the cDNA probe. By DNA sequencing, fragments of the human genomic DNA that code for amino acids at both the amino and carboxylterminal regions of human $\alpha_1$-antitrypsin were identified. The distance between these two regions is approximately 5 kb, which is in good agreement with our estimates of the size of the gene, based on the electron micrographs. The amino acid sequence at the amino-terminal region agrees for 30 of the 33 residues that have been published for human $\alpha_1$-antitrypsin (Morii et al., J. Biochem. (1978) 83:269–277). Amino acids that are different include $Lys_{10}$, $His_{20}$ and $Ile_{26}$, which were reported as Glu, Set and Leu, respectively The DNA sequence corresponding to the amino-terminal region of the protein was confirmed by sequencing both strands of the geomic DNA. Furthermore, the residues in question are identical to those determined for baboon $\alpha_1$-antitrypsin. The amino acid sequence containing 32 residues at the carboxyl end of the mature protein was also deduced from the genomic DNA sequence. This amino acid sequence is in complete agreement with that previously published for $\alpha_1$-antitrypsin (Carrell et al., Biochem. Biophys. Res. Comm. (1979) 91:1032–1037). Also, the genomic DNA sequence was identical with the corresponding nucleotide sequence of a human $\alpha_1$-antitrypsin cDNA clone.

The first ATG start codon at the 5' end of the $\alpha_1$-antitrypsin gene is located 24 amino acids upstream from the amino-terminal Glu residue in the mature protein. This region appears to code for a typical signal peptide, which is removed from the mature protein during intracellular processing prior to extracellular transport. The features of this signal peptide are similar to those seen for other signal peptides including an amino terminal methionine residue, a hydrophobic core flanked by regions of more polar residues, a small uncharged amino acid at the putative cleavage site, proline at position −5 and a length of ∼15–30 amino acid residues. Furthermore, there appears to be a "TATA box" sequence located at position −25 to −31 of the gene, which resembles the consensus sequence $TATA_{ATA}{}^{TAT}$, proposed by Cordon et al. Science (1980) 209:1406–1414. The transcription start point in eukaryotes also has a consensus sequence, PyCAPyPyPyPyPy (A=position +1; Py represents pyrimidine).

Based on the description in Kurachi et al, (1981), supra, the baboon $\alpha_1$-antitrypsin gene can also be used for producing baboon $\alpha_1$-antitrypsin as described above in conjunction with the disclosure of Kurachi.

In accordance with the subject invention, $\alpha_1$-antitrypsin can be produced by hybrid DNA techniques. By virtue of the flexibility of hybrid DNA technology, large amounts of $\alpha_1$-antitrypsin free of sugar substituents can be obtained. Furthermore, by employing appropriate hosts, the presence of the leader peptide allows for secretion of the product into the nutrient medium for ease of isolation.

Although the foregoing invention has been described in some detail by way of illustration and example for purposes of clarity of understanding, it will be obvious that certain changes and modifications may be practiced within the cope of the appended claims.

What is claimed is:

1. An isolated nucleic acid consisting of the human $\alpha_1$-antitrypsin cDNA sequence shown in FIGS. 1A–1K.

2. A host cell transformed with a nucleic acid according to claim 1.

3. A vector comprising a nucleic acid according to claim 1.

4. A host cell transformed with a vector according to claim 3.

* * * * *

UNITED STATES PATENT AND TRADEMARK OFFICE
CERTIFICATE OF CORRECTION

PATENT NO. : 5,399,684
DATED : March 21, 1995
INVENTOR(S) : E.W. Davie et al.

It is certified that error appears in the above-indentified patent and that said Letters Patent is hereby corrected as shown below:

| COLUMN | LINE | |
|---|---|---|
| [56] (pg. 1, col. 2) | Refs. Cited Publications | Insert --Carrell et al., Biochem. Biophys. Res. Commun. (1979) 91:1032-1037-- |
| [56] (pg. 1, col. 2) | Refs. Cited Publications | Insert --Mega et al., J. Biol. Chem. (1980) 255:4057-4061.-- |
| [56] (pg. 1, col. 2) | Refs. Cited Publications | Insert --Crawford, Arch. Biochem. Biophys. (1973) 156:215-222.-- |
| [56] (pg. 1, col. 2) | Refs. Cited Publications | Insert --Chandra et al., Biochem. Biophys. Res Commun. (1981) 103:751-758.-- |
| [56] (pg. 1, col. 2) | Refs. Cited Publications | Insert --Woo et al., Induction and cloning of the $\alpha_1$-antitrypsin gene, *Federation Proceedings* 40(6):1754, Abstract No. 1240, May 1, 1981.-- |
| [56] (pg. 1, col. 2) | Refs. Cited Publications | Insert --Davie, E.W., Cloning of fibrinogen, prothrombin, and $\alpha_1$-antitrypsin, The Harvey Lectures, Series 77, Academic Press, New York, pp. 1-21, 1983.-- |
| [56] (pg. 1, col. 2) | Refs. Cited Publications | Insert --Kurachi et al., Isolation and characterization of a cDNA clone coding for $\alpha_1$-antitrypsin, Abstract N. 0255, Eight International Conference on Thrombosis and Haemostatis, 14 July 1981.-- |

UNITED STATES PATENT AND TRADEMARK OFFICE
CERTIFICATE OF CORRECTION

PATENT NO. : 5,399,684            Page 2 of 4

DATED : March 21, 1995

INVENTOR(S) : E.W. Davie et al.

It is certified that error appears in the above-indentified patent and that said Letters Patent is hereby corrected as shown below:

| COLUMN | LINE | |
|---|---|---|
| [56] (pg. 1, col. 2) | Refs. Cited Publications | Insert --Woo et al., The human alpha-1-antitrypsin gene pulmonary emphysema, Abstract No. 7061, Twenty-first Annual Meeting of the American Society for Cell Biology, November 9-13, 1981.-- |
| [56] (pg. 1, col. 2) | Refs. Cited Publications | Insert --Davie et al., The structure and cloning of the $\alpha_1$-antitrypsin, gene, *Protein, Nucleic Acid and Enzyme* 27(12):1805-1809, 1982, based on a lecture in November 1981.-- |
| [56] (pg. 1, col. 2) | Refs. Cited Publications | Insert --Kurachi et al., Cloning and nucleotide sequences of cDNA and genomic DNA coding for $\alpha_1$-antitrypsin, *Fed. Proc.* 41:517, Abstract No. 1446, April 15-23, 1982.-- |
| [56] (pg. 1, col. 2) | Refs. Cited Publications | Insert --Colten, H.R., et al., Genetics and biosynthesis of complement proteins, *New Engl. J. of Med.* 304:653-456, 1981.-- |
| [56] (pg. 1, col. 2) | Refs. Cited Publications | Insert --Colten, H.R., et al., Synthesis and secretion of complement proteins by macrophages, *Annals New York Academy of Sciences* 332:482-490, 1979.-- |
| [56] (pg. 1, col. 2) | Refs. Cited Publications | Insert --Reid, K.B.M., et al., The proteolytic activation systems of complement, *Ann. Rev. Biochem.* 50:433-464, 1981.-- |

UNITED STATES PATENT AND TRADEMARK OFFICE
CERTIFICATE OF CORRECTION

PATENT NO. : 5,399,684
DATED : March 21, 1995
INVENTOR(S) : E.W. Davie et al.

It is certified that error appears in the above-indentified patent and that said Letters Patent is hereby corrected as shown below:

| COLUMN | LINE | |
|---|---|---|
| 1 | 54 | "Conunun." should read --Commun.-- |
| 1 | 55 | "Biol. Chem." should read --J. Biol. Chem.-- |
| 1 | 56 | "Blochem." should read --Biochem.-- |
| 1 | 60 | "Blochem." should read --Biochem.-- |
| 2 | 59 | "bacterial" should read --bacteria-- |
| 3 | 16 | "reticulocytelysate" should read --reticulocyte lysate-- |
| 4 | 39 | "-antitrypsin" should read --$\alpha_1$-antitrypsin-- |
| 4 | 67 | "pBalal" should read --pBa$\alpha$lal-- |
| 5 | 52-53 | "humangeonomic" should read --human geonomic-- |
| 5 | 58 | "carboxylterminal" should read --carboxy-terminal-- |

UNITED STATES PATENT AND TRADEMARK OFFICE
CERTIFICATE OF CORRECTION

PATENT NO. : 5,399,684
DATED : March 21, 1995
INVENTOR(S) : E.W. Davie et al.

It is certified that error appears in the above-indentified patent and that said Letters Patent is hereby corrected as shown below:

| COLUMN | LINE | |
|---|---|---|
| 6 | 3 | "Set" should read --Ser--. |

Signed and Sealed this

First Day of October, 1996

Attest:

BRUCE LEHMAN

*Attesting Officer*     *Commissioner of Patents and Trademarks*